US010545213B2

(12) United States Patent
 Krellmann

(10) Patent No.: US 10,545,213 B2
(45) Date of Patent: Jan. 28, 2020

(54) METHOD AND MAGNETIC RESONANCE APPARATUS FOR AVOIDING ACQUISITION OF DATA IN EXAMINATION REGIONS EXHIBITING HIGH DISTORTION

(71) Applicant: Siemens Healthcare GmbH, Erlangen (DE)

(72) Inventor: Christof Krellmann, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/128,738

(22) Filed: Sep. 12, 2018

(65) Prior Publication Data

US 2019/0079156 A1    Mar. 14, 2019

(30) Foreign Application Priority Data

Sep. 12, 2017    (DE) .................. 10 2017 216 051

(51) Int. Cl.
 *G01R 33/565* (2006.01)
 *A61B 5/055* (2006.01)
 (Continued)

(52) U.S. Cl.
 CPC ...... *G01R 33/56572* (2013.01); *A61B 5/0555* (2013.01); *A61B 5/743* (2013.01);
 (Continued)

(58) Field of Classification Search
 CPC ............... A61B 5/055; G01R 33/5608; G01R 33/56518; G01R 33/56563; G01R 33/4818
 See application file for complete search history.

(56) References Cited

U.S. PATENT DOCUMENTS

2006/0012365 A1\*  1/2006  Werthner ........... G01R 33/4833
                                                324/307
2014/0296697 A1\*  10/2014  Fenchel ............... A61B 5/0035
                                                600/411

(Continued)

FOREIGN PATENT DOCUMENTS

DE    10 2005 030 795 A1    7/2006
EP         3 309 574 A1    4/2018

OTHER PUBLICATIONS

German Office Action dated Jul. 26, 2019, for Application No. 10 2017 216 051.9.

*Primary Examiner* — Alesa Allgood
(74) *Attorney, Agent, or Firm* — Schiff Hardin LLP

(57) ABSTRACT

In a method for operating a magnetic resonance (MR) apparatus, at least one first distortion-corrected MR image is displayed at a display screen, with a first selection symbol superimposed thereon for selection of a scan volume from which diagnostic MR data are to be subsequently acquired. A second MR image is also displayed, that is at least partially distorted, and which represents at least a part of the region encompassed by the first distortion-corrected MR image. The second MR image is superimposed with a second selection symbol that indicates the same scan volume defined by the first selection symbol, but in the second magnetic resonance image. The second selection symbol is then used by an operator to select the actual scan volume from which the diagnostic MR data will be acquired, and a magnetic resonance apparatus is operated to acquire the MR data from that selected scan volume.

13 Claims, 4 Drawing Sheets

(51) Int. Cl.
*A61B 5/00* (2006.01)
*G01R 33/483* (2006.01)

(52) U.S. Cl.
CPC ........ *A61B 5/7435* (2013.01); *G01R 33/4835* (2013.01); *A61B 5/7425* (2013.01)

(56) References Cited

U.S. PATENT DOCUMENTS

2017/0069107 A1\* 3/2017 Kobayashi ............ G06T 19/006
2017/0242089 A1\* 8/2017 Kiefer .................. G01R 33/443
2018/0333069 A1\* 11/2018 Paul ....................... A61B 5/055

\* cited by examiner

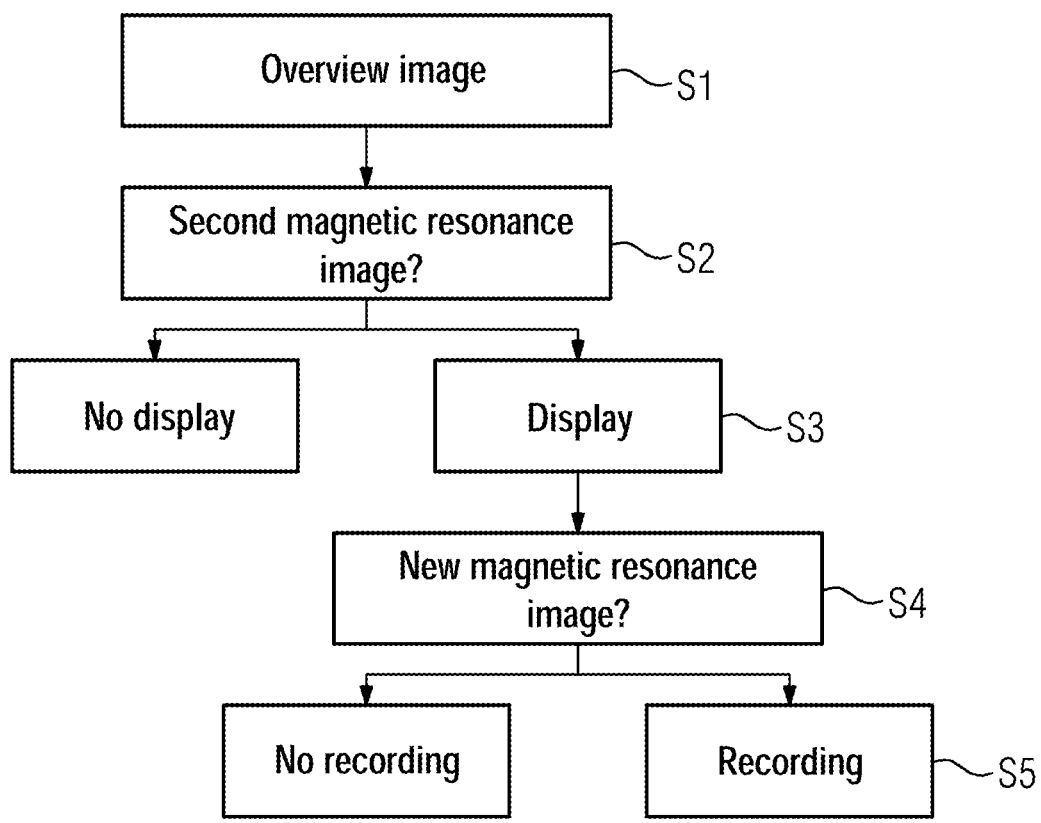

METHOD AND MAGNETIC RESONANCE APPARATUS FOR AVOIDING ACQUISITION OF DATA IN EXAMINATION REGIONS EXHIBITING HIGH DISTORTION

BACKGROUND OF THE INVENTION

Field of the Invention

The present invention concerns a method and apparatus for designating a region for acquiring magnetic resonance data from a subject that allow avoiding selection of a region wherein high distortions fields exist.

Description of the Prior Art

In order to record magnetic resonance (MR) images, patients are moved into a magnetic resonance scanner while being supported on a patient bed. In this process, the bed position can be adjusted in the magnetic resonance scanner even before entry into the magnetic resonance scanner, so that the examination region is located in the homogeneous region of the basic magnetic field of the scanner.

After positioning the patient bed, the basic magnetic field is homogenized. Overview images are then acquired. These are used in order to check the position of the patient and to specify recording slices for subsequent scans. If flow measurements at the aorta are to be performed, the image plane must lie perpendicular to the aorta. Even small deviations corrupt the scan results.

With spectroscopic examinations, however, in some cases it is essential for scan signals to originate only from a defined tissue region. If signal contributions from other tissues appear, the diagnostic value of signal relationships between different peaks can be corrupted.

The overview images may be obtained in different ways. This may involve multiple individual images. For example, this may involve three individual images that are perpendicular to one another may be obtained.

Alternatively, a 3D data record may be acquired, in order to generate arbitrary sectional images therefrom as overview images.

Ultimately, the positioning of subsequent magnetic resonance images is carried out on the basis of one or more overview images. In this context, the overview images are superimposed on a display screen with a selection symbol. This selection symbol shows the scan volume in the section with the image. Usually, it has a square-shaped or rectangular shape, depending on the direction.

The selection symbol can be moved translationally or rotationally, in order to specify the scan slice. It is also possible to specify the length and width of the scan slice. Conventionally, the limits defined by the magnetic resonance scanner or the scan parameters are monitored while doing so. For example, the thickness of a scan slice has a minimum value that can be achieved, which depends upon the pulse shape of the radio-frequency pulse during the application of the slice selection gradient and the gradient strength in this direction.

If the overview images lie in regions in which the magnetic field gradients are no longer homogeneous, then the images appear distorted in these regions. Since the gradient field strengths can be ascertained, it is possible to correct such distorted images. These images are then distortion-corrected. The distortions contained in the images are considerable for some scans, but not for others. Spectroscopic scans, for example, are highly susceptible to distortions. The user cannot, however, identify where the distortions become too large.

The positioning of the scan volume, also referred to as the scan slice, often takes place manually. This is because the placement and number of scan slices or scan volumes depends upon a number of boundary conditions, and on the other hand automation with sufficient accuracy for all issues is not available.

A user who wishes to carry out a positioning manually is shown a distortion-corrected image as an overview image in each case. Because of the distortion-correction, regions of the overview image in which significant distortion exists can no longer be recognized by the user. In some positions and scan methods, this results in the scan volume being selected so as to be in a region in which it is not desirable for the scan volume to be for good image quality.

SUMMARY OF THE INVENTION

An object of the present invention is to provide a method and an MR apparatus with which an improved positioning accuracy is enabled.

The above object is achieved In accordance with the present invention by a method for operating a magnetic resonance apparatus wherein at least one first distortion-corrected magnetic resonance image is displayed at a display screen, with a first selection symbol superimposed thereon for selection of a scan volume from which diagnostic magnetic resonance data are to be subsequently acquired. Further in accordance with the invention, at least one second magnetic resonance image is displayed, that is at least partially distorted, and which represents at least a part of the region encompassed by the first distortion-corrected magnetic resonance image. The second magnetic resonance image is superimposed with a second selection symbol that indicates the same scan volume that was defined by the first selection symbol, but in the second magnetic resonance image. The second selection symbol is then used by an operator to select the actual scan volume from which the diagnostic magnetic resonance data are to be acquired, and this selected scan volume is embodied in a scan protocol that is used to operate the magnetic resonance apparatus, i.e., the scanner thereof, in order to acquire the magnetic resonance data from the selected scan volume.

The most important insight involved in the invention is considered to be not changing the display of the overview image. This is represented in a distortion-corrected manner as usual, with a selection symbol superimposed thereon. In order to also obtain a precise positioning in difficult cases, in addition to displaying the overview image as the first magnetic resonance image, at least one second magnetic resonance image is displayed that is not distortion-corrected. This shows the examination region from the gradient perspective, so to speak.

A second selection symbol is superimposed on the second magnetic resonance image. The second selection symbol indicates the same scan volume that was defined by the first selection symbol. In this context, the selection symbols are always mapped as cross-sections in the represented plane.

By viewing the second magnetic resonance image and the second selection symbol, the user can immediately and precisely identify whether or not the scan volume that has been selected includes unwanted regions.

If the scan volume includes regions that are not to be included in the scan, the user can modify the scan volume via the first selection symbol and thus correct the size or the position of the scan volume. Alternatively, the second selection symbol can also be editable, in order to modify the position of the scan volume by doing so.

The scan volume can be a single slice or multiple slices. In a scan volume with multiple slices, it is advantageous for these to have the same slice thickness and to be aligned parallel with each other. In principle, however, the slices can be positioned freely.

MR scanner can be provided with one or more display devices. If a number of display devices are assigned to a single magnetic resonance scanner, the display of the two magnetic resonance images and the two selection symbols preferably takes place on the same display device.

The second magnetic resonance image shows at least the region of the first magnetic resonance image in which the first selection symbol lies. Preferably, the first and the second magnetic resonance images map the same examination region. The resolution may differ, however. The orientation is preferably identical. Alternatively, the orientation of the second magnetic resonance image may depend upon or be identical to the orientation of the selection symbol.

The first magnetic resonance image is preferably an overview image. In principle, however, it may be any possible magnetic resonance image.

The solution according to the invention offers several advantages. The first, as described, is that the positioning accuracy is increased. The second is that the standard workflow does not need to be revised, but rather only needs to be supplemented. The display of the first magnetic resonance image thus can take place as usual. The user does not need to accept any loss of the usual information that is available from viewing the first magnetic resonance image.

Preferably, the second magnetic resonance image and the second selection symbol are displayed as a function of the position of the first selection symbol. In particular, the second magnetic resonance image and the second selection symbol may then be displayed if the first selection symbol lies at least partially in a region of the first magnetic resonance image that is distortion-corrected. The second magnetic resonance image and the second selection symbol are therefore displayed only if the slice position is affected by a non-linearity of a gradient field. Otherwise, the additional display does not offer relevant information, and would be confusing.

Here, the display of the second magnetic resonance image and the second selection symbol may depend upon the strength of the distortion. Therefore, these are not displayed for every small distortion, but only when a threshold value is exceeded.

The threshold value may be specified by image regions of the first magnetic resonance image. If the first selection symbol falls at least partially or entirely within one of these regions, the second magnetic resonance image and the second selection symbol are displayed, and otherwise not.

Preferably, an information field is also displayed along with the display of the second magnetic resonance image. Particularly in the embodiment where the second magnetic resonance image is not always displayed together with the first, the display of the second magnetic resonance image may confuse the user. The information field may then clarify to the user that the selected slice lies in a region with non-linear gradients and the second magnetic resonance image can offer support with fine positioning.

In the simplest embodiment, the first magnetic resonance image may be used to produce the second magnetic resonance image, if the first image is not distortion-corrected during this processing. The second magnetic resonance image may, however, also involve any other magnetic resonance image. If a highly precise positioning is required, the second magnetic resonance image may advantageously be recorded after a modification of a property of the first selection symbol. It then maps the examination region precisely as it is at the moment of the positioning.

Alternatively, at least one navigator echo may also be recorded, and the representation of the second magnetic resonance image adapted as a function of the navigator echo. Smaller changes can be mapped in this manner. As a function of the change in position of the examination region ascertained from the navigator echo(es), this may also prompt the recording of a second magnetic resonance image. In this context, the non-linearity of the gradient fields or, more generally, the strength of the cause of the distortion, may be taken into consideration.

Furthermore, second magnetic resonance images may be recorded and represented continuously, independently of modifications to the first or second selection symbol. This then takes place in "real time". The second magnetic resonance images are thus exchanged at regular intervals, for example 1 second. This takes place until the one scan is started or the slice positioning is interrupted in some other way.

If the recording of a magnetic resonance image is involved, this naturally means that raw data are recorded and processed to form an image. In doing so, different processing steps can be carried out. It is therefore possible to obtain the first and the second magnetic resonance image from the same raw data. When processing the first magnetic resonance image, the step of distortion correction is applied, but not when processing the second magnetic resonance image.

If the second magnetic resonance image is recorded separately or after a movement of the first image or even the second selection symbol, the resolution of the second magnetic resonance image may be lower than that of the first magnetic resonance image. As a result, the second magnetic resonance image is recorded more rapidly.

In this context, depending on the structure to be examined, a higher resolution than that of the first magnetic resonance image may alternatively be used. If the first magnetic resonance image is a standard overview image, in addition to the distortion correction it may also have a resolution that is too low for the diagnosis that is desired to be made. In this case, the second magnetic resonance image may be recorded such that it has an adequate resolution.

As a further alternative, the first magnetic resonance image and the second magnetic resonance image may have the same resolution.

The resolution of the second magnetic resonance image may be selected as a function of the size and/or position of the scan volume and thus as a function of the size and/or position of the first selection symbol. This can take place automatically. With very small scan volumes, such as with spectroscopy scans, a high resolution may be used, and vice versa.

Preferably, in order to record the second magnetic resonance image, a sequence of the group turbo spin echo, FLASH or TrueFISP can be used. Furthermore, any other sufficiently fast scan sequence can be used, with which a magnetic resonance image is able to be recorded and processed after a movement or other change to the first or second selection symbol. In this context, a time period of less than one to a few seconds is targeted. Otherwise, too much time passes after a change to the selection symbol in order to be able to carry out the slice positioning smoothly.

The displaying of the second magnetic resonance data record and the second selection symbol should therefore optimally take place "on the fly" (dynamically). Changes are to be represented immediately, so as not to incorrectly position the scan volume.

Preferably, after each change to a property of the first selection symbol or the second selection symbol, a second magnetic resonance image can be recorded and represented superimposed by a second selection symbol. This is primarily advantageous with strong distortions. Alternatively, the second magnetic resonance image can be recorded if the modification exceeds a threshold value. Properties may be the position or the size of the scan volume and thus of the first selection symbol. Here as well, this may involve a volume, although the first magnetic resonance image is only superimposed by a surface. As stated, this involves only the cross-section in the slice represented.

The first selection symbol is preferably designed as a rectangle, in particular as a square, or as a grid. These are common shapes for such a selection symbol.

The second selection symbol may likewise be designed as a rectangle, in particular as a square, or as a grid. Preferably, however, the second selection symbol is distorted as a function of the distortion of the first magnetic resonance image. The second selection symbol is thus represented in the manner in which the first selection symbol is distorted by the distortion during the scan. This is based on the idea that a distortion can in fact be subtracted out from an image. If, however, the scan volume contains undesirable regions due to the distortion, these often cannot be corrected any more. Thus, although the representation of the first magnetic resonance image can be corrected, this is not possible for a spectroscopy scan with undesirable signal components.

When superimposing the second magnetic resonance image with the second selection symbol, this is preferably be taken into consideration in order to further increase the positioning accuracy. The greater the distortion, the greater too the distortion of the scan volume. Accordingly, the distortion of the second selection symbol can also be carried out as a function of the strength of the distortion at the location of the scan volume.

Preferably, the distortion of the second selection symbol is implemented in a location-dependent manner. For example, the second selection symbol is distorted to a greater degree, the further it is removed from the center of the homogeneous region.

The distortion of the second selection symbol may be implemented as a function of at least one gradient-based parameter. If the distortions are a result of non-linearities of the gradient fields, these can be represented mathematically and calculated, or at least indicated. They can therefore also be taken into consideration when calculating the distortion of the second selection symbol.

The distortion of the selection symbol can be implemented as a function of the bed position of the patient bed. The bed position can be used as a measure for gradient-based distortions. The distortion is thus also location-dependent.

Preferably, the distortion of the selection symbol is implemented as a function of at least one physical parameter of the examination object. For example, the so-called chemical shift leads to a shifting of fat signals with respect to water signals. Susceptibility jumps in the examination object act as gradients and thus likewise lead to incorrect encodings of the location information and even to signal cancellations.

Preferably, the distortion of the selection symbol is implemented as a function of at least one scan sequence-dependent parameter. Distortions of this kind, which result from calculable distortions due to the structure of the scan sequence, are able to be acquired mathematically and, as a result, reproduced particularly precisely.

Depending upon the embodiment of the magnetic resonance image data record, distortions of the selection symbol are possible in two or three spatial directions.

The distortion of the second selection symbol can be implemented in the phase direction. Additionally or alternatively, a distortion can be carried out in the read direction. Additionally or alternatively, the distortion can be carried out in the slice selection direction. The distortion is added in the directions in which it occurs as a result of gradients or other factors.

If desired, distortions can be represented and superimposed on the second magnetic resonance image only in two spatial directions. A number of individual magnetic resonance images or slices, or magnetic resonance images of a three-dimensional image data record can be used, however, in order to specify a scan volume. In doing so, all three spatial directions or gradient directions can also be taken into overall consideration.

Of course, it is also possible to use second magnetic resonance images that are not positioned precisely in the read and phase directions or the slice selection direction. The distortion is then obtained by a projection of the phase, read and slice selection direction onto the direction of the magnetic resonance image.

Preferably, the distortion of the second selection symbol is obtained by an inversion of the distortion correction of the first magnetic resonance image. This results in the location dependency of the correction being preserved.

The first selection symbol and/or the second selection symbol can be used to select a scan volume for a spectroscopic scan. In certain cases, it is crucial to keep the scan free from interference signals. Particularly for spectroscopic scans, a diagnostic result is often obtained by the relationship between the signal intensities of two peaks. If one of the two peaks is influenced by a signal outside the desired region, the corrupted relationship is unusable. The method according to the invention thus provides benefits for spectroscopic scans in particular.

The present invention also encompasses a magnetic resonance apparatus having a control computer that is programmed or designed or configured to operate the magnetic resonance apparatus, or the scanner thereof, in order to implement any or all embodiments of the method according to the invention, as described above.

The present invention also encompasses a non-transitory, computer-readable data storage medium encoded with programming instructions that, when the storage medium is loaded into a computer or computer system of magnetic resonance apparatus, cause the computer or computer system to operate the magnetic resonance apparatus in order to implement any or all embodiments of the method according to the invention as described above.

The method can be implemented in the control apparatus as software or as (hard-wired) hardware (circuitry).

Embodiments of the data carrier, and the magnetic resonance apparatus according to the invention correspond to the embodiments of the method according to the invention.

BRIEF DESCRIPTION OF THE DRAWINGS

FIG. 7 is a flowchart of a modification of the embodiment of FIG. 6.

DESCRIPTION OF THE PREFERRED EMBODIMENTS

Figure 1:
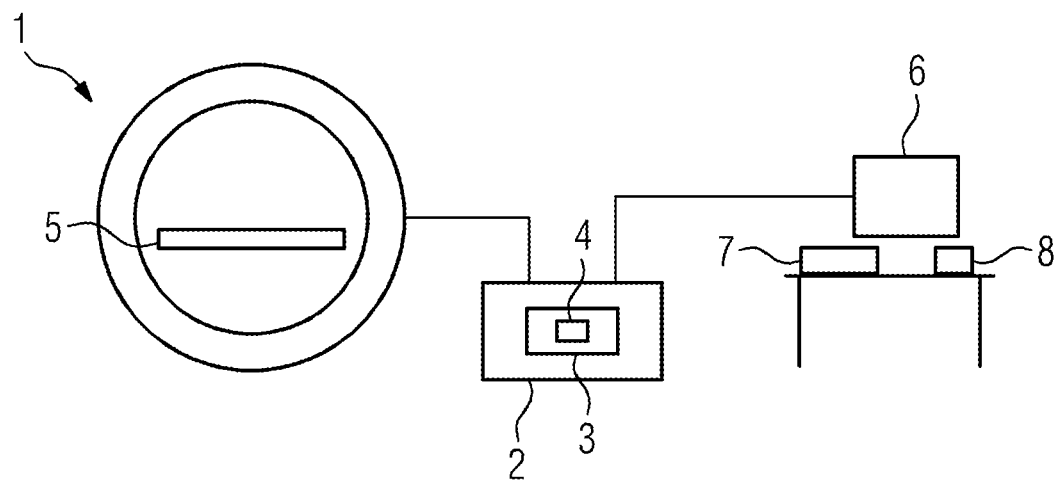
FIG. 1 schematically illustrates a magnetic resonance apparatus.

FIG. 1 shows a magnetic resonance apparatus 1. A control computer 2 is provided for controlling the scanner 1A of the magnetic resonance apparatus 1.

The magnetic resonance apparatus 1 further has a data carrier 3. The data carrier 3 can be embodied as part of the control computer 2 or independently thereof, so as to be loadable into the control computer 2. Stored on the data carrier 3 is computer code 4 for performing magnetic resonance scans and otherwise implementing the inventive method.

Furthermore, the magnetic resonance apparatus 1 has a patient bed 5, on which a patient can be supported. This can be moved in the longitudinal direction of the scanner 1A.

The magnetic resonance apparatus 1 is assigned at least one display device 6 and at least two input devices 7 and 8. The display device 6 is also designated as a monitor. The input device 7 can be a keyboard and the input device 8 can be a computer mouse.

Figure 2:
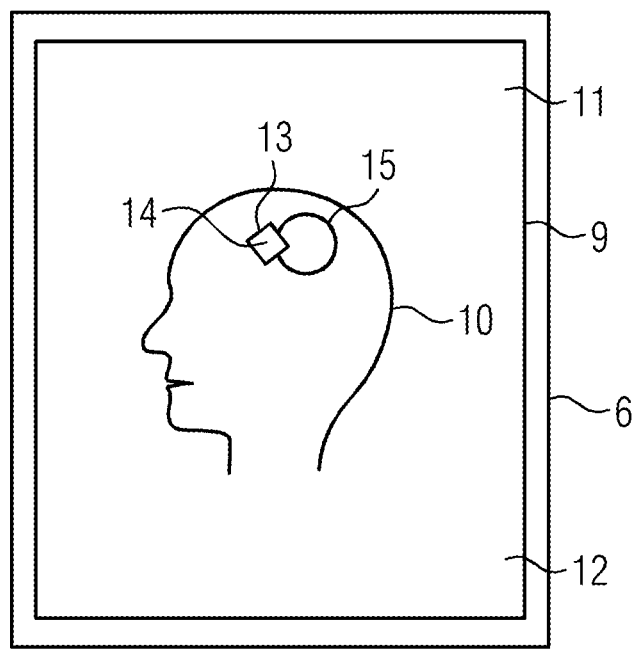
FIG. 2 shows an overview image with a selection symbol according to the prior art.

FIG. 2 shows a known first magnetic resonance image 9, which is used as an overview image. This is represented on the display device 6. The first magnetic resonance image 9 maps an examination region 10 in the form of a head. The first magnetic resonance image 9 is distorted as a result of non-linearities of the imaging gradients in a first region 11, and undistorted in a second region 12. These regions transition into one another smoothly. No sharp boundary lines are indicated, since their location is dependent upon a distortion threshold value to be stipulated, for example. The distortion in the first region 11 is location-dependent and increases, the further the distance from the center which is located at the level of the chest of the patient. The first magnetic resonance image 9 is distortion-corrected, for which reason no distortion can be identified.

The first magnetic resonance image 9 is superimposed with a first selection symbol 13, with which the scan volume 14 of a spectroscopic scan can be specified. The first selection symbol 13 has a square cross-section in the chosen direction. The first selection symbol 13 is designed as a frame, so that the contents of the enclosed scan volume 14 can be identified. In another view, the first selection symbol 13 can also be designed as a rectangle. The scan volume 14 then has the shape of a cuboid.

If the first selection symbol 13, and thus the scan volume 14, lies in the first region 11, then the scan volume 14 may also include a region 15, which is not to be scanned and that introduces the interference signal into the scan signals. With spectroscopic scans, the region 15 is a region that has different tissue than the scan volume 14, and which thus would corrupt signal intensities in the spectrum to be generated.

Figure 3:
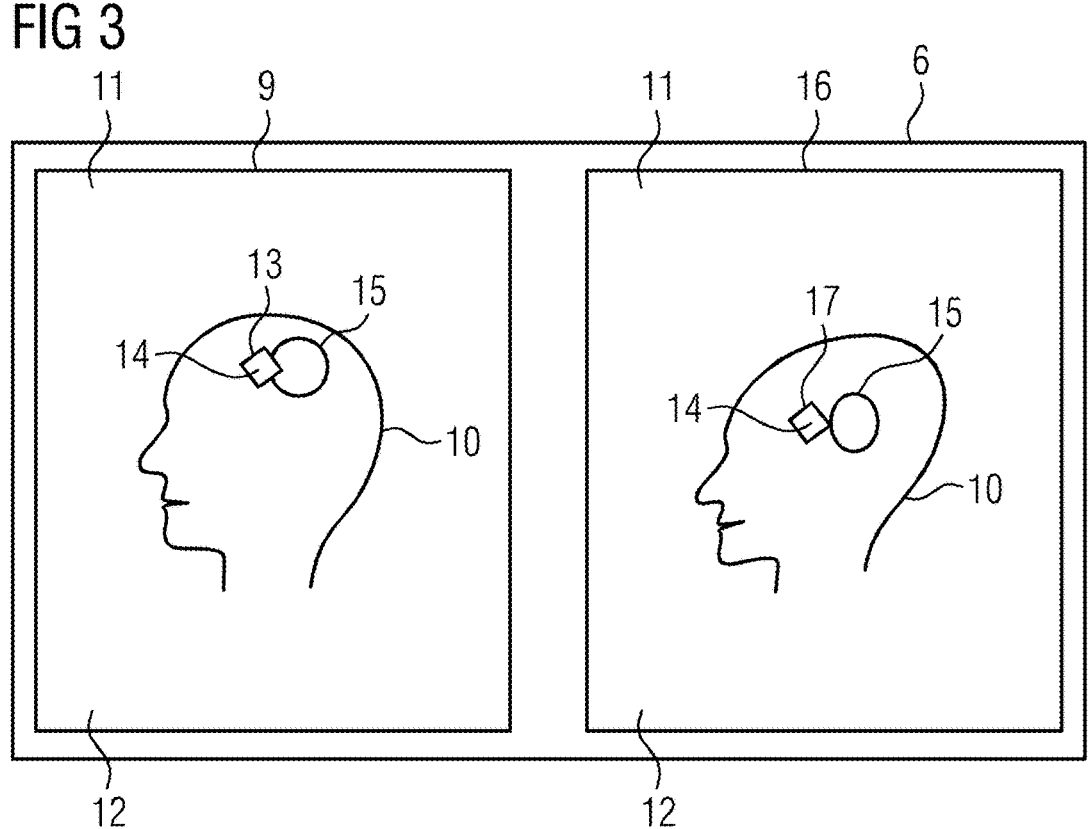
FIG. 3 shows two magnetic resonance images in a first embodiment of the invention.

FIG. 3 shows the first magnetic resonance image 9 with a superimposed first selection symbol 13. In addition, a second magnetic resonance image 16 is represented on the display device 6, which is superimposed by a second selection symbol 17. The second magnetic resonance image 16 maps the examination region 10 without distortion correction.

The second selection symbol 17 can be represented in exactly the same way as the first selection symbol 13, i.e. as a square or rectangle.

By representing the second magnetic resonance image 16 without correction, it is possible to better identify whether the scan volume 14 is correctly placed in borderline situations. Thus, on the basis of the second magnetic resonance image 16, it is possible to identify that the scan volume 14 does not lie in the region 15.

Figure 4:
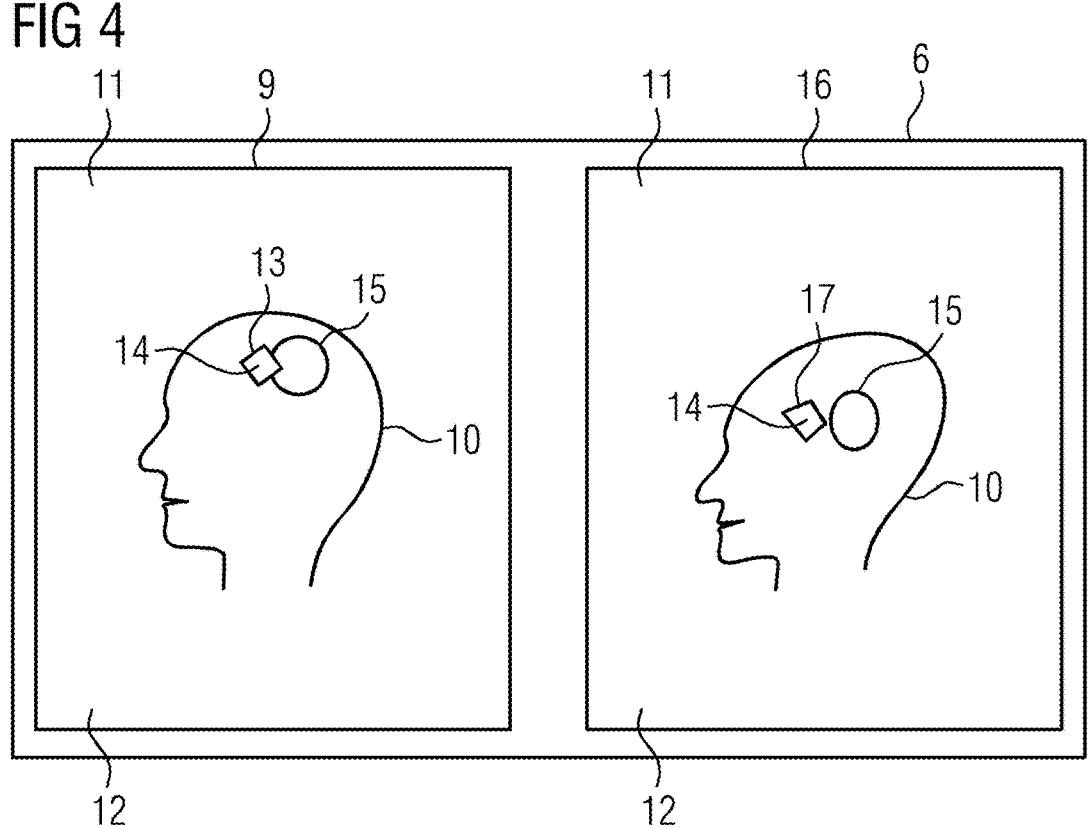
FIG. 4 shows two magnetic resonance images in a second embodiment of the invention.

FIG. 4 shows modified version of FIG. 3. In this case, the second selection symbol 17 is adapted to the distortions. This is advantageous in particular for distortions which shift the scan region 14 by more than a voxel's width. For smaller shifts, there is no need for any adaptation and a rectangular representation is sufficient.

Figure 5:
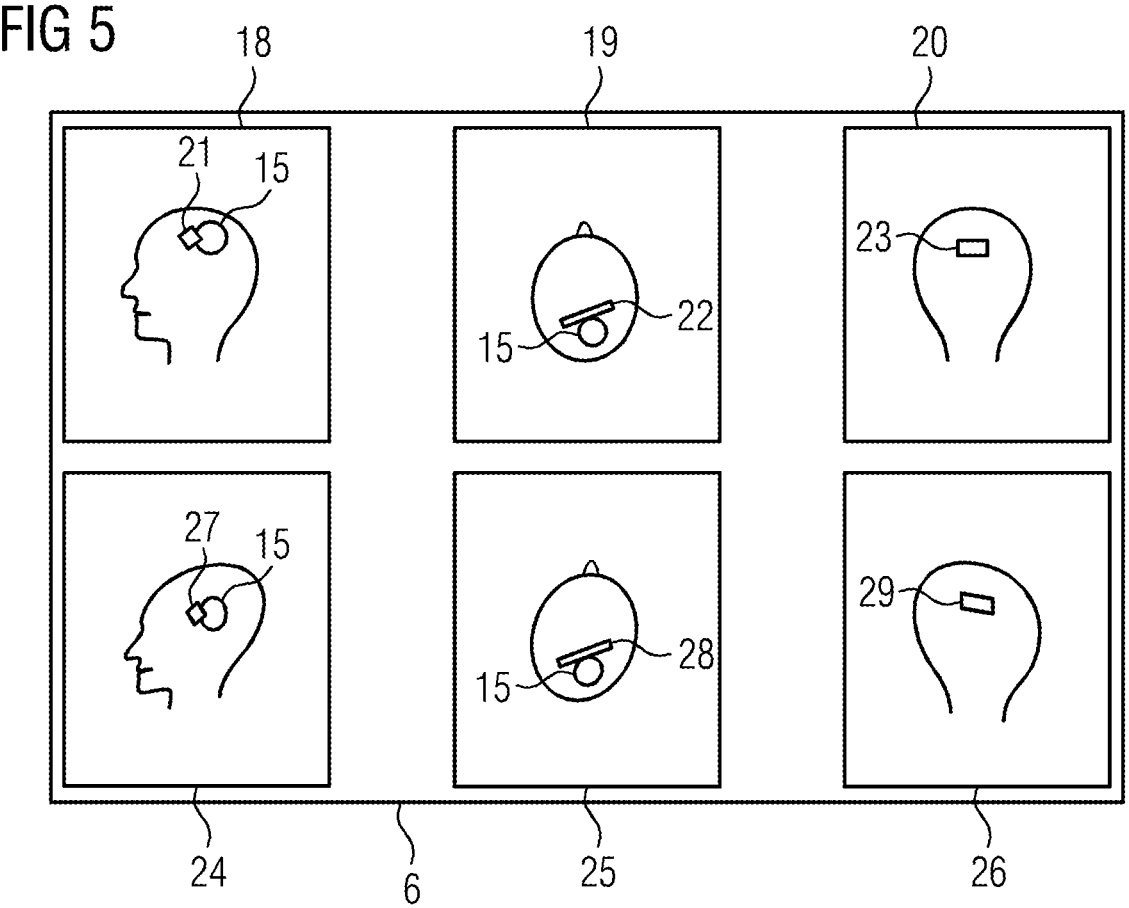
FIG. 5 shows a number of magnetic resonance images in a third embodiment of the invention.

FIG. 5 shows an embodiment of the invention. Here, a number of first magnetic resonance images 18, 19 and 20 are represented with selection symbols 21, 22 and 23 superimposed. The first magnetic resonance image 18 shows the examination region in a sagittal sectional direction, the first magnetic resonance image 19 in the transverse direction and the first magnetic resonance image 20 in the frontal plane. Here, the first magnetic resonance images 18, 19 and 20 are distortion-corrected.

Accordingly, second magnetic resonance images 24, 25 and 26 are displayed, which likewise map the examination region 10 in the sagittal, transverse and frontal directions. The second magnetic resonance images 24, 25 and 26 are not distortion-corrected. Superimposed on the second magnetic resonance images 24, 25 and 26 are second selection symbols 27, 28 and 29. Each of these show the location of the scan volume 14, which is defined by the first selection symbols 21, 22 and 23, in a magnetic resonance image which is not distortion-corrected. The second selection symbols 27, 28 and 29 may likewise be represented in a distorted manner.

Figure 6:
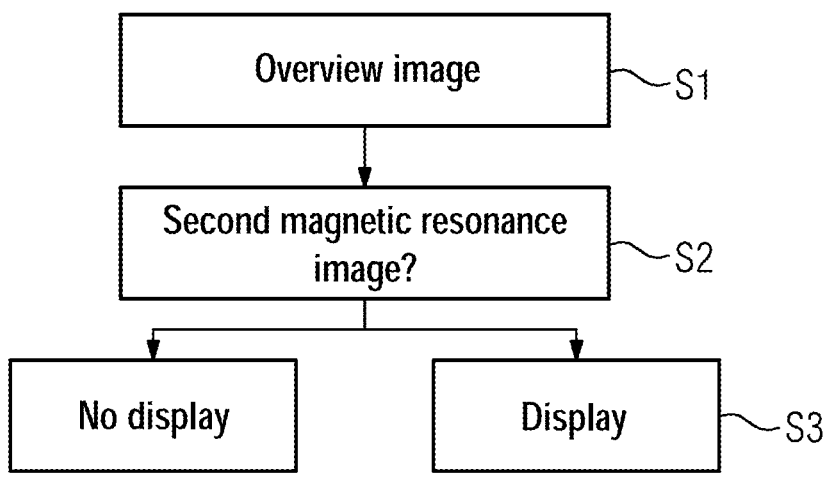
FIG. 6 is a flowchart of an embodiment of the method of the invention.

FIG. 6 shows a flowchart for the operation of a magnetic resonance apparatus 1. In step S1, a first magnetic resonance image 9 is displayed as an overview image on the display device 6. The first selection symbol 13 is placed in the center of the first magnetic resonance image 9 as standard.

In step S2, it is specified whether the second magnetic resonance image 16 is to be represented. The first selection symbol 13 and thus also the scan volume 14 either lies in an undistorted region 12 of the first magnetic resonance image 9, in which case a second magnetic resonance image 16 is not displayed.

The first selection symbol may also lie partially or entirely in a distorted region of the first magnetic resonance image 9. In this case, the second magnetic resonance image 16, superimposed by the second selection symbol 17, is represented as step S3. When the position of the first selection symbol 13 is changed, this decision is made repeatedly.

FIG. 7 shows a development of the flowchart according to FIG. 6. In this context, after one of the properties of the first selection symbol 13 is changed, it is decided whether a more recent second magnetic resonance image 16 is recorded as step S4. If at least one threshold value is exceeded, a second magnetic resonance image 16 is recorded and represented in the display device 6 together with the first magnetic resonance image 9. In each case, the two are superimposed by a selection symbol 13 and 17, respectively.

In this context, the intermediate step may also be dispensed with and whenever a property or a property from a specific group is changed, a second magnetic resonance image 16 can always be recorded and displayed.

If more than one first magnetic resonance image 9 is displayed, then the decision loops are run through for each first magnetic resonance image 18, 19 and 20. It may then be specified, how to proceed, if the scan volume 14 lies in a distorted region in only one or two first magnetic resonance images 18, 19 and 20. In a first alternative, all second magnetic resonance images 24, 25 and 26 and the respective second selection symbols 27, 28 and 29 are always displayed. In a second alternative, second magnetic resonance images 24, 25 or 26 are only displayed for those first magnetic resonance images 18, 19 or 20, in which the first selection symbol 20, 21 or 22 and thus the scan volume 14 lies in a distorted region.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for operating a magnetic resonance (MR) apparatus, comprising:
   at at least one display screen in communication with a computer, displaying a distortion-corrected first MR image that represents an examination region of a subject from which MR diagnostic data are to be acquired;
   at said at least one display screen using said computer to superimpose a first selection symbol on said distortion corrected first magnetic resonance image for use in selecting a scan volume from which said MR diagnostic data are to be acquired;
   at said at least one display screen, displaying an at least partially distorted second MR image that represents at least a portion of the examination region represented in said distortion-corrected first MR image;
   using said computer to superimpose a second selection symbol on the at least partially distorted second MR image, said second selection symbol being superimposed at a position on said at least partially distorted second MR image that corresponds to a position of the scan volume selected with said first selection symbol, and thereby representing the position of said scan volume in said at least partially distorted second MR image;
   using said second selection symbol to make an entry into said computer that selects the scan volume for acquiring said MR diagnostic data and, in said computer, including a designation of the selected scan volume in control signals for operating said MR apparatus; and
   from said computer, operating said MR apparatus according to said control signals to acquire said MR diagnostic data from the scan volume selected using said second selection symbol.

2. A method as claimed in claim 1 comprising operating said MR apparatus to acquire said at least partially distorted second MR image after a change to a property of said first selection symbol.

3. A method as claimed in claim 1 comprising, after each change to a property of said first selection symbol, operating said MR apparatus to acquire the at least partially distorted second MR image.

4. A method as claimed in claim 1 comprising operating said MR apparatus to acquire said at least partially distorted second MR image repeatedly at predetermined intervals.

5. A method as claimed in claim 1 comprising representing said second selection symbol on said at least one display screen on said at least partially distorted second MR image so as to be distorted dependent on distortion that was corrected in order to produce said distortion-corrected first MR image.

6. A method as claimed in claim 1 comprising superimposing said second selection symbol on said at least partially distorted second MR image with a distortion of said second selection symbol that is location-dependent.

7. A method as claimed in claim 1 wherein said at least partially distorted second MR image comprises distortions that occur due to at least one gradient-based parameter of a gradient system of said MR apparatus.

8. A method as claimed in claim 1 comprising superimposing said second selection symbol on said at least partially distorted second MR image with a distortion obtained by inversion of a distortion correction that was used to produce said distortion corrected first MR image.

9. A method as claimed in claim 1 comprising displaying said at least partially distorted second MR image with a resolution that is lower than a resolution of said distortion-corrected first MR image.

10. A method as claimed in claim 1 comprising operating said MR apparatus to acquire said at least partially distorted second MR image by executing an MR data acquisition sequence selected from the group consisting of a turbo spin echo sequence, a FLASH sequence, and a TrueFISP sequence.

11. A method as claimed in claim 1 comprising using said first selection symbol to select said scan volume in order to select an examination region for acquiring spectroscopic data as said diagnostic MR data.

12. A magnetic resonance (MR) apparatus comprising:
   an MR data acquisition scanner;
   a computer in communication with at least one display screen, said computer being configured to display, at said at least one display screen, a distortion-corrected first MR image that represents an examination region of a subject from which MR diagnostic data are to be acquired;
   said computer being configured to superimpose a first selection symbol on said distortion corrected first magnetic resonance image at said at least one display screen, for use in selecting a scan volume from which said MR diagnostic data are to be acquired;
   said computer being configured to display, at said at least one display screen, an at least partially distorted second MR image that represents at least a portion of the examination region represented in said distortion-corrected first MR image;
   said computer being configured to superimpose a second selection symbol on the at least partially distorted second MR image at said at least one display screen, said second selection symbol being superimposed at a position on said at least partially distorted second MR image that corresponds to a position of the scan volume selected with said first selection symbol, and thereby representing the position of said scan volume in said at least partially distorted second MR image;
   said computer being configured to receive an entry via said second selection symbol that selects the scan volume for acquiring said MR diagnostic data, and said computer being configured to include a designation of the selected scan volume in control signals for operating said MR apparatus; and said computer being configured to operate said MR apparatus according to said control signals to acquire said MR diagnostic data from the scan volume selected using said second selection symbol.

13. A non-transitory, computer-readable data storage medium encoded with programming instructions, said storage medium being loaded into a computer system of a magnetic resonance (MR) apparatus, and said programming instructions causing said computer system to:

at at least one display screen in communication with said computer system, display a distortion-corrected first MR image that represents an examination region of a subject from which MR diagnostic data are to be acquired;

at said at least one display screen, superimpose a first selection symbol on said distortion corrected first magnetic resonance image for use in selecting a scan volume from which said MR diagnostic data are to be acquired;

at said at least one display screen, display an at least partially distorted second MR image that represents at least a portion of the examination region represented in said distortion-corrected first MR image;

at said at least one display screen, superimpose a second selection symbol on the at least partially distorted second MR image, said second selection symbol being superimposed at a position on said at least partially distorted second MR image that corresponds to a position of the scan volume selected with said first selection symbol, and thereby representing the position of said scan volume in said at least partially distorted second MR image;

receive, via said second selection symbol, an entry that selects the scan volume for acquiring said MR diagnostic data, and include a designation of the selected scan volume in control signals for operating said MR apparatus; and operate said MR apparatus according to said control signals to acquire said MR diagnostic data from the scan volume selected using said second selection symbol.

\* \* \* \* \*